United States Patent
Van Baalen et al.

(10) Patent No.: US 6,319,666 B1
(45) Date of Patent: Nov. 20, 2001

(54) INDUCTION OF REV AND TAT SPECIFIC CYTOTOXIC T-CELLS FOR PREVENTION AND TREATMENT OF HUMAN IMMUNODEFICIENCY VIRUS (HIV) INFECTION

(75) Inventors: Carel A. Van Baalen, Zeewolde; Albertus D.M.E. Osterhaus, Bunnik, both of (NL)

(73) Assignee: Erasmus Universiteit Rotterdam, Rotterdam (NL)

( * ) Notice: Subject to any disclaimer, the term of this patent is extended or adjusted under 35 U.S.C. 154(b) by 0 days.

(21) Appl. No.: 09/284,651
(22) PCT Filed: Oct. 17, 1997
(86) PCT No.: PCT/IB97/01402
§ 371 Date: Jun. 17, 1999
§ 102(e) Date: Jun. 17, 1999
(87) PCT Pub. No.: WO98/17309
PCT Pub. Date: Apr. 30, 1998

Related U.S. Application Data

(63) Continuation-in-part of application No. 08/733,789, filed on Oct. 18, 1996, now Pat. No. 6,024,965.

(51) Int. Cl.$^7$ ............ C12Q 1/70; A61K 39/21; C07H 21/04; C07K 16/00
(52) U.S. Cl. ........ 435/5; 424/208.1; 536/23.72; 530/388.75
(58) Field of Search ........ 424/208.1; 536/23.72; 530/388.75; 435/5

(56) References Cited

U.S. PATENT DOCUMENTS

| | | | |
|---|---|---|---|
| 5,336,758 | 8/1994 | Berzofsky et al. | 530/326 |
| 5,439,809 | 8/1995 | Haynes et al. | 435/69.3 |

FOREIGN PATENT DOCUMENTS

WO 94 15634  7/1994  (WO) .

OTHER PUBLICATIONS

Klein, M. R., F. Miedema, *Trends in Microbiology* 3, 386 (1995).
Keet, I. P. M. et al, *AIDS* 7, 51 (1993).
Haynes, B. F et al., *Science* 271, 324 (1996).
Nixon, D. F. et al., *Nature* 336, 484 (1988).
Walker, B. D. et al, *Science* 240, 64 (1988).
Buseyne, F. et al., *J. Virol.* 67. 694 (1993).
Riviere , Y. et al, *J. Virol.* 63, 2270 (1989).
Koup, R. A. et al, *Blood* 73, 1909 (1989).
Johnson R. P. et al.,*Curr. Top. Microbiol. Immunol.* 189, 35 (1994).
Lamhamedi–Cherradi, S. et al, *AIDS* 6, 1249 (1992).
Lamhamedi–Cherradi, S. et al,*AIDS* 9, 421 (1995).
Riviere, Y. et al., *Curr. Top Microbiol. Immunol.* 189, 65 (1994).
Rinaldo, C. et al. *J. Virol* 69, 5838 (1995).
Carmichael, A. et al, *J. Exp. Med.* 177, 249 (1993).

(List continued on next page.)

*Primary Examiner*—Hankyel T. Park
(74) *Attorney, Agent, or Firm*—Sim & McBurney

(57) ABSTRACT

The presence of cytotoxic T-cells to the Rev and/or Tat protein in samples from a subject infected with immunodeficiency virus, particularly HIV in humans, is an indication of a stable disease condition and a favorable prognosis of lack of progression to disease. Immunogenic compositions containing at least one cytotoxic T-cell epitope of the Rev and/or Tat protein of an immunodeficiency virus, particularly HIV, or a vector encoding the T-cell epitope, may be used to prevent infection by disease caused by the immunodeficiency virus, by stimulating, in the host, a specific cytotoxic T-cell response specific for the respective Rev and/or Tat proteins.

14 Claims, 3 Drawing Sheets

OTHER PUBLICATIONS

Koup, R. A. et al., *Journal of Virology* 68, 4650 (1994).
Klein, M. R. et al,*J. Exp. Med.* 181, 1365 (1995).
Geretti, A M. et al, *J. Inf. Dis.* 174, 34 (1996).
Mellors, J. W. et al, *Science* 272, 1167 (1996).
Jurrianns, S. et al., et al, *Virol.* 204, 223 (1994).
E. Hogervest, et al, *J. Infect. Dis* 171, 811 (1995).
J.W. Mellors, et al, *Ann. Intern. Med.* 122, 573 (1995).
D.R. Henrard, et al, *JAMA* 274, 554 (1995).
K. Sasela, S.E. Stevens, P. Rubinstein, P.E. Taylor, D. Baltimore, *Ann. of Intern. Med.* 123, 641 (1995).
van Baalen, C. A., et al, *AIDS* 7, 781 (1993).
Culmann–Penciolelli, B. el al, *J Virol.* 69, 618 (1995).
Culmann, B. et al, *Eur. J. Immunol.* 19, 2382 (1989).
Seshamma, T. et al, *Proc. Natl. Acad.* vol. 89, 10663–10667, 1992.
Embretson, J. et al. *Nature* 359 (1993).
Hope, T. et al,*Curr Top Microbiol. Immunol.* 193, 91 (1995).
Ranki, A. et al., *Arch Virol.* 139, 365 (1994).
Blazevic, V. et al., *AIDS Res. Hum. Retroviruses* 11, 1335 (1995).
Zinkernagel, R. M.et al., *J. Exp. Med.* 145, 644 (1977).
Ulmer et al., (1993) *Curr. Opinion Invest. Drugs.* 2 (9): 983–989.
Hope T., et al., Current topics in Microbiology and Immunology 193: 91–105.
Gayner R.B 1995, Current Topics in Microbiology and Immunology 193: 51–77.
Moss B., Science, vol. 252, pp. 1662–1667 (Jun. 1991).
Baxby, D. et al., Vaccine vol. 10, Issue 1, 1992.
Gönczol, E. et al, Vaccine, vol. 13, No. 12, pp. 1080–1085, 1995.
Imler, Jean–Lue, Vaccine vol. 13, No. 13, pp. 1143–1151, 1995.

Sztein, M.B. et al., The Journal of Immunology, 1995, 155: pp. 3987–3993.
Aldovini, A. et al., Nature (1991), vol. 351: 479–482.
Shiver, J.W. et al., Annals New York Academy of Sciences, pp. 198–208.
Chai, S.K. et al, The Journal of Immunology, vol. 149:2385–2390, No. 7, Oct. 1, 1992.
Sauzet, J.P. et al., Vaccine, Vo.. 13, No. 14, pp. 1339–1345, 1995.
Zhou, F. et al., The Journal of Immunology, vol. 149, 1599–1604, No. 5, Sep. 1, 1992.
Takahashi, H. et al., Nature, vol. 344:873–875, Apr. 26, 1990.
Voge et al., Vaccine Design, Ed. Powell et al, 1995, chapter 7, pp. 141–228.
Moore, A. et al., Vaccine, vol. 13, No. 18, pp. 1741–1749, 1995.
Adams, S. E., Vaccine Research, vol. 2: 163–172, No. 3, 1993.
Rammensee, H. G. et al.; Immunogenetics 41, 178–228, 1995.
Liljestrom, P., Biotechnology, vol. 9 (1991), 1356–1361.
Warner, J. et al., J. Cell Biochem. Supp. vol. 0, No. 21B 228, 1995.
Riviere, Y, et al., Aids Research and Human Retroviruses, vol. 11, N o. 4, 481–489, 1995.
Liberman, J. et al, Aids Research and Human Retroviruses, vol. 13, No. 5, 383–392, 1997.
Choppin J. et al., J. Immun. 147, 575–583, 1991.
van Baaken, C. et al., J. of Gen. Virology, vol. 78, No. 8, 1913–1918, 1997.
Tsuji, T,. et al., Immunology, vol. 90, No. 1, 1–6, 1997\.

| LTA | progressors: |
|---|---|
| 1) L090 | 8) P493 |
| 2) L658 | 9) P1215 |
| 3) L211 | 10) P356 |
| 4) L709 | 11) P424 |
| 5) L434 | 12) P039 |
| 6) L008 | |
| 7) L157 | |

INDUCTION OF REV AND TAT SPECIFIC CYTOTOXIC T-CELLS FOR PREVENTION AND TREATMENT OF HUMAN IMMUNODEFICIENCY VIRUS (HIV) INFECTION

REFERENCE TO RELATED APPLICATION

This application is a continuation-in-part of U.S. patent application Ser. No. 08/733,789 filed Oct. 18, 1996 now U.S. Pat. No. 6,024,965.

FIELD OF THE INVENTION

The present invention is related to the field of immunology and is particularly concerned with methods and compositions for the induction of cytotoxic T-cells to prevent and treat human immunodeficiency virus (HIV) infection and AIDS.

BACKGROUND TO THE INVENTION

It is believed that most people with HIV infection will ultimately develop clinical AIDS. Furthermore, death from the complications of AIDS often occurs within months or years after clinical AIDS is diagnosed. Most HIV-infected individuals remain healthy for many years despite the infection. Likewise, some individuals with past clinical diagnosis continue to live productive lives for many years after first developing clinical AIDS.

Among HIV-1 infected individuals, the duration of the asymptomatic period after seroconversion may differ considerably (refs. 1 to 3—throughout this specification, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure). Mechanisms suggested to play a role in long-term survival include viral characteristics, as well as host genetic and immunological factors. However, immunological correlates of AIDS-free survival have not been conclusively identified (refs. 1 and 3).

The human immunodeficiency virus type 1 (HIV-1) and related lentiviruses have more complex genomes than typical retroviruses. In addition to the gag, pol and env genes common to all retroviruses, HIV-1 also encodes genes for tat, rev, nef, vif, vpu, and vpr. The HIV-1 protein Rev (regulator of expression of the virion) plays an essential role in the temporal regulation of virus gene expression during a replication cycle. The genes expressed by HIV-1 can be separated into two groups based on whether their expression is Rev-dependent or not. The Rev-independent or early genes encode Tat, Rev, and Nef. The Rev-dependent or late genes are important for virion production and encode the structural proteins Gag, Pol and Env and the accessory products Vif, Vpu and Vpr. Rev is absolutely required for HIV-1 replication. Proviruses that lack Rev function remain transcriptionally active, but fail to generate new viral particles. The biology of the Rev protein is summarized in reference 30.

Cis- and trans-acting elements which regulate HIV gene expression have been identified. An 86 amino acid viral protein, Tat is required for HIV-1 gene expression and for subsequent viral replication. Tat is unique among viral transactivators. Unlike E1A and Tax, which activate a number of viral and cellular genes, Tat activation is relatively specific for HIV-1. A cis-acting element in the HIV-1 LTR, located downstream of the RNA initiation site, is critical for high-level gene expression. This element, which extends from +1 to +60 in the HIV-1 LTR, was designated the trans-acting response element, or TAR. TAR forms a double-stranded RNA structure which is required for high-level gene expression in response to Tat. The function of Tat is described in reference 31.

The present invention is concerned with the role of HIV-1 specific cytotoxic T lymphocytes (CTL) in AIDS-free long-term survival of HIV-1 infected individuals. In previous studies, CTL specific for the structural proteins Gag and RT have been detected in at least 80% of seropositive individuals (refs. 4 to 9), whereas CTL against Nef and Vif have been reported in approximately 50% of seropositive individuals (refs. 10 to 12). These studies have also indicated that the regulatory proteins Rev and Tat are less frequently recognized (refs. 10 to 12). Cross-sectional studies have shown that HIV-1 specific CTL precursors (CTLp) are generally present in the asymptomatic stage, but their frequencies tend to be low in advanced disease (refs. 13, 14). Longitudinal analyses have shown that HIV-1 specific CTL responses are associated with initial control of viremia (ref. 15) and that Gag specific CTLp decline with disease progression, probably as a result of HIV-1 induced $CD4^+$ cell decline (refs. 16, 17) and cytokine dysfunction (ref. 17). Viral loads have been shown to be predictive of disease progression and can be measured by commercially available tests (refs. 18, 19).

Furthermore, there are no commercially available immunological tests to determine favorable prognosis of a patient infected with HIV.

There is a need for laboratory tests that identify those HIV-infected individuals who are more likely to have a favorable prognosis, slower disease progression, and stable disease compared with those individuals who are likely to have poor prognosis, or more rapid disease progression.

Infection with HIV leads to a serious immunodeficiency disease, AIDS. There is no cure for AIDS nor is there any vaccine against infection and the disease. It would be desirable to provide methods and compositions (including immunogenic compositions, such as vaccines) for the prevention and treatment of AIDS. It would also be desirable to provide test procedures and materials to identify those patients who are likely to have a favourable prognosis and a slower disease progression.

SUMMARY OF INVENTION

The present invention is concerned with the diagnosis of the disease condition of a host infected by immunodeficiency virus, particularly humans infected by human immunodeficiency virus and, in particular, to the identification of immunological correlation of AIDS-free survival following HIV infection. Such identification leads to the provision of immunogenic compositions and immunization procedures which can prevent progression to AIDS in seropositive HIV patients.

The inventors have found that the presence of Rev and Tat specific CTL precursors during the asymptomatic stage of infection is correlated with AIDS-free survival, while no such correlation was found for CTL precursors of other HIV proteins, including Gag, RT and Nef, indicating that CTL responses against Rev and/or Tat are important for protection from disease progression.

In one aspect of the present invention, there is provided an immunogenic composition effective for preventing disease caused by infection by an immunodeficiency virus, particularly a human immunodeficiency virus, which comprises at least one T-cell epitope selected from the Rev and Tat proteins of the immunodeficiency virus or a vector encoding the at least one cytotoxic T-cell epitope.

The at least one cytotoxic T-cell epitope may be from the Rev protein, the Tat protein or from both the Rev and Tat proteins. The cytotoxic T-cell epitope may be provided by the Rev and/or Tat protein or a homolog thereof in which amino acids have been deleted, inserted or substituted without essentially detracting from the immunological properties thereof, generally in combination with a pharmaceutically-acceptable carrier therefor.

The at least one cytotoxic T-cell epitope also may be provided by a recombinant vector, such as a recombinant virus vector, such as a recombinant vaccinia or Semliki virus, or a non-replicating vector encoding the at least one cytotoxic T-cell epitope, which encode the Rev and/or Tat protein of HIV or other immunodeficiency virus or a homolog thereof in which amino acids have been deleted, inserted or substituted without essentially detracting from the immunological properties thereof.

The at least one cytotoxic T-cell epitope further may be provided by a synthetic peptide having an amino acid sequence corresponding to the T-cell epitope or a homolog thereof in which amino acids have been deleted, inserted or substituted without essentially detracting from the immunological properties thereof, generally in combination with a pharmaceutical carrier therefor.

The present invention further comprises a method of immunizing a host against disease caused by infection by an immunodeficiency virus, particularly HIV, which comprises stimulating, in the host, a cytotoxic T-cell response which is specific for the Rev and/or Tat proteins of the immunodeficiency virus. The stimulation of the cytotoxic T-cell response may be effected by administering to the host at least one T-cell epitope selected from the Rev and Tat protein of HIV or other immunodeficiency virus or- a vector encoding the at least one T-cell epitope. Such T-cell epitope or vector encoding the same may be provided in any of the manners described above.

In an additional aspect of the present invention, there is provided a method of immunizing a host against disease caused by infection by immunodeficiency virus, specifically human immunodeficiency virus, which comprises selectively stimulating a protective Rev and/or Tat protein-specific cytotoxic T-cell response in the host. The selective stimulation of the protective cytotoxic T-cell response may be achieved by administering to the host at least one T-cell epitope selected from Rev and Tat protein of HIV. The administration of the T-cell epitope may be effected by any of the procedures described above.

The discoveries made by the inventors further lead, in accordance with an additional aspect of the invention, to a method of determining a favourable prognosis in an HIV-positive subject, which comprises detecting in the subject the presence of a cytotoxic T-cell response to the Rev and/or Tat protein of HIV as an indication of the favourable prognosis.

In addition, the present invention provides a method of diagnosing a stable disease condition associated with HIV in a human, which comprises:

obtaining peripheral blood mononuclear cells from the human, and testing the sample for the presence of a specific cytotoxic T-cell response to Rev and/or Tat proteins as an indication of the stable disease condition.

The present invention extends to at least one cytotoxic T-cell epitope selected from the Rev and Tat proteins of HIV or a vector encoding the at least one cytotoxic T-cell epitope when used as a medicament. The invention further includes the use of at least one cytotoxic T-cell epitope selected from the Rev and Tat proteins of HIV or a vector encoding the at least one cytotoxic T-cell epitope in the manufacture of a medicament, particularly a medicament for immunizing a host against disease caused by HIV by stimulating a specific cytotoxic T-cell response which is specific to the Rev and/or Tat proteins of HIV or by selectively stimulating a protective Rev and/or Tat protein-specific cytotoxic T-cell response in the host. The cytotoxic T-cell epitope may be provided in any of the manners described above.

BRIEF DESCRIPTION OF THE FIGURES

The above disclosure generally describes the present invention which will be further understood from the following general description with reference to the drawing in which.

GENERAL DESCRIPTION OF THE INVENTION

Figure 1A:
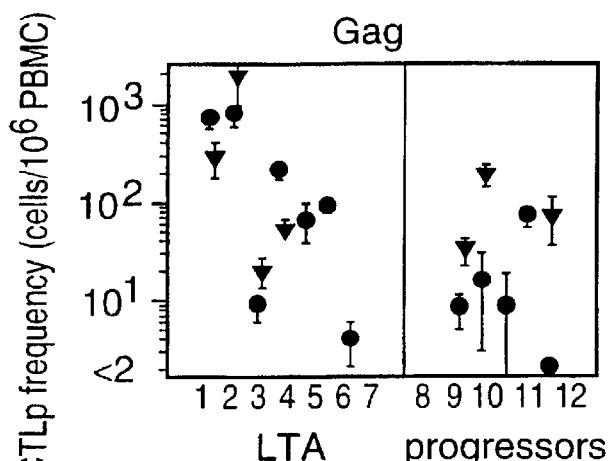
FIG. 1, comprising five panels, shows the frequency of CTL precursors specific for the HIV-1 proteins, Gag, RT, Nef, Rev and Tat in the asymptomatic stage of seven long term asymptomatics (LTA) and five progressors.
Figure 1B:
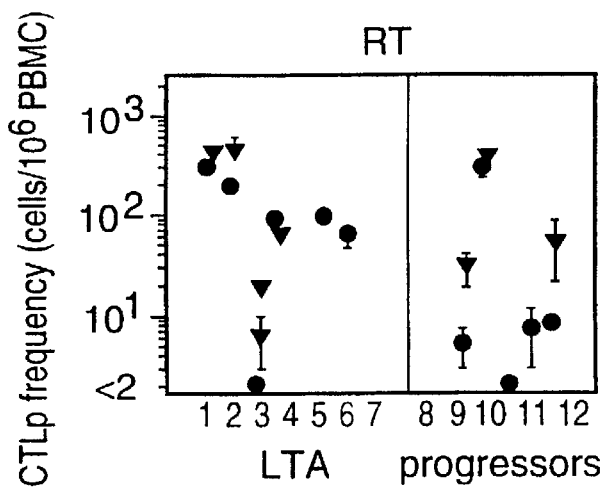
Figure 1C:
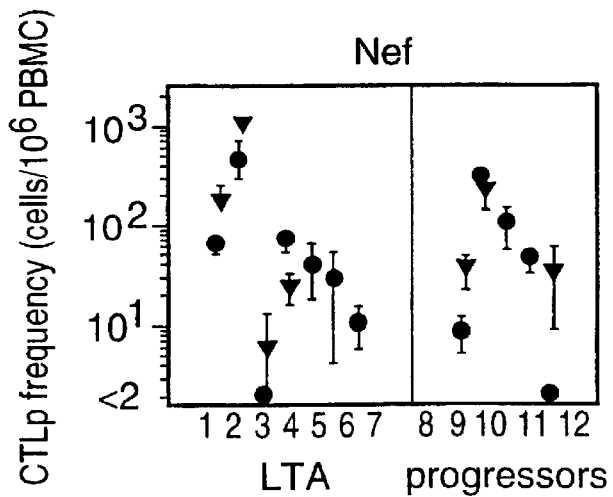
Figure 1D:
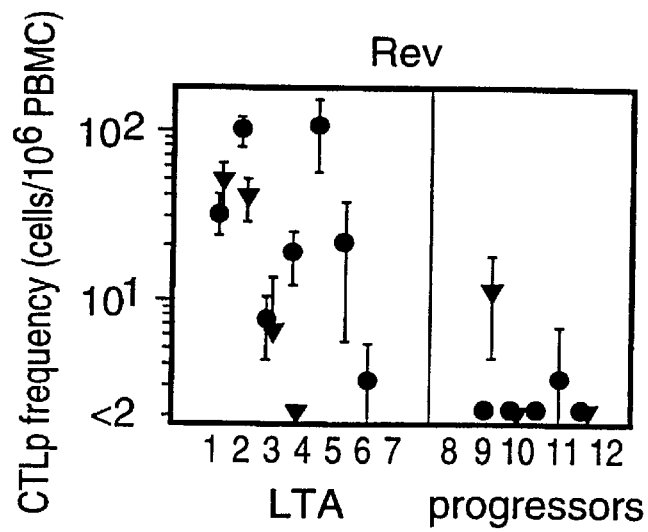
Figure 1E:
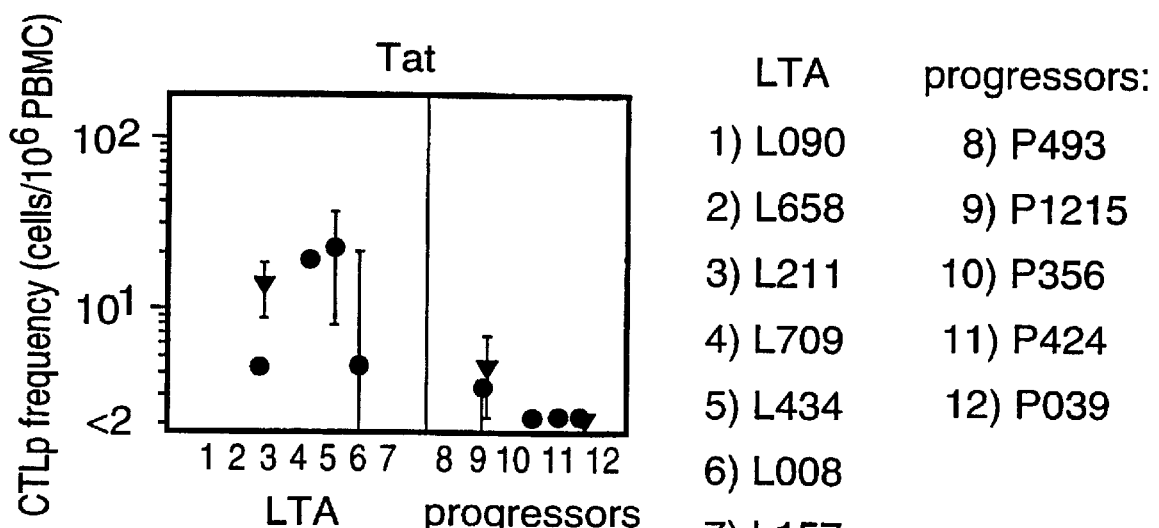

In one aspect, the present invention provides a method for preventing immunodeficiency disease mediated by an immunodeficiency virus in a host by inducing in the host cytotoxic T-cells specific for Rev and Tat proteins of the immunodeficiency virus.

The desirability of inducing such Rev- and Tat- specific cytotoxic T-cells was -discovered, in part, by an analysis of the immune status of HIV-infected individuals. The characteristics of the HIV-1 seropositive individuals are shown in Table I below. All progressors and four out of seven long term asymptomatics (LTA) were seronegative at entry. Intervals between the last seronegative and first seropositive visit (seroconversion interval) were small allowing a well defined estimate of the time of seroconversion calculated at the midpoint between these two visits. AIDS defining symptoms of the progressors were Karposi's sarcoma (P493), Candida albicans Desoptagitis (P1215, P424 and P039), and, Pneumocystis carinii pneumonia (P356). Rates of CD4 cells cediae (s.opes) were calculated from CD4 cell counts measured at regular three month intervals during the entire follow up period. For L008 and P1215 (see Table I), AZT therapy was started at 109 and 51 months after entry, respectively, and DDC therapy was started at 126 and 69 months, respectively. The other individuals did not receive anti-viral therapy. Time points of PBMC sampling for CTL precursors (CTLp) frequency analysis, and their corresponding CD4 counts are indicated (in Table I). HLA-A and -B phenotypes of the individuals were serologically determined. The frequencies of CTLp to the five HIV-1$_{lai}$ proteins, Gag, RT, Nef, Rev and Tat were retrospectively determined in the asymptomatic stage of twelve seropositive individuals. Participants of the Amsterdam Cohort studies on AIDS were selected from the Amsterdam Cohort of Homosexual (ACH) men on the basis of their rate of disease progression and HLA class I phenotype. Seven of these individuals remained AIDS-free for more than a decade (median 129 months, range 110 to 140 months) after seroconversion or entry in the study (LTA: L090, L658, L211, L709, L434, L008, L157). The other five progressed to AIDS within 3 to 6 years (median 47 months, range 39 to 72 months) after seroconversion (progressors: P493, P1215, P356, P424, P039). To minimize the influence of HLA-polymorphism on the results of CTL measurements, individuals were selected with matched HLA class I alleles: for each LTA, except L008 and L157, there was found at least one progressor sharing three of the HLA-A and -B alleles (see Table I).

The rate of CD4 cell decline with time differed among individuals within each group (see Table I). Among the LTA, L090 had a slight but progressive increase of 1.1 cells $ml^{-1}$ $month^{-1}$ and was considered a "true non-progressor" (ref. 1). CD4 cell numbers declined slowly in L658 (−1.3), and moderately in L211, L709 and L434 (−3.1, −3.5 and −3.7, respectively). The decline was more pronounced in L008 and L157 (−4.5 and −5.6 respectively). Their CD4 counts were lower than 200 cells $ml^{-1}$ at 132 and 130 months after entry, respectively, and continued to decline until the end of the study in the absence of symptoms. Among the progressors, the CD4 cell decline was slow in P493 (−3.1), more pronounced in P1215 and P356 (−4.4 and −7, respectively), and rapid in P424 and P039 (−14 and −19, respectively). Mean HIV-1 RNA serum levels measured within the first year after seroconversion, ranged from <$1.0 \times 10^3$ copies $ml^{-1}$ for three of the four LTA who were seroegative at entry in the study (Table 1). In the fourth, L658, these levels dropped to a stable level of <$1.0 \times 10^3$ copies $ml^{-1}$ within 34 months after seroconversion. The means HIV-1 RNA serum levels in progressors ranged from $1.9 \times 10^4$ to $4.7 \times 10^5$ copies $ml^{-1}$ in this period.

Retrospective CTLp frequency analyses were performed on PBMC that had been cryopreserved at time points when all the individuals were still asymptomatic with CD4 counts about 400 cells $ml^{-1}$ (see Table I). Only P1215 entered the study with CD4 counts below 400 cells $ml^{-1}$. CTLp frequencies were measured according to previously established methods (refs. 17, 20). Samples from each progressor were tested in parallel with those from one or more LTA. CTLp frequencies differed considerably among individuals within each group (see FIG. 1). FIG. 1 shows the frequencies of CTLp against HIV-1 Gag, RT, Nef, Rev and Tat detected in the asymptomatic stage of seven LTA and five progressors.

Cultures were established as described previously (refs. 16, 17, 20), using cryopreserved PBMC sampled from LTA and progressors at time points indicated in Table I. Briefly, PBMC were stimulated in vitro in different dilutions for 14 to 20 days in vitro with paraformaldehyde fixed autologous B lymophoblastoid cell lines infected with recombinant vaccinia viruses VVTG1144 (Gag), VVTG4163 (RT), VVTG1147 (Nef), VVTG4113 (Rev) and VVTG3196 (Tat), kindly provided by Dr. M. P. Kieny (Transgene, Strasbourg, France). CTL assays and precursor frequency calculations were performed as described previously (ref. 17). Progressor samples were tested in parallel to those of LTA with at least three matching HLA-A and -B alleles. Differences in CTLp frequencies between the LTA and progressor groups were analyzed with the Mann-Whitney Wilcoxson ranking test.

Rev and Tat specific CTLp were found predominantly in LTA, whereas CTLp directed against Gag, RT or Nef were found at frequencies that were similar in individuals of -both groups. The latter observation illustrates that the absence of detectable Rev and Tat specific CTL in progressors could not be attributed to a general failure of CTL induction in vivo.

The only progressor P493 who did exhibit Rev and Tat specific CTLp albeit at low frequencies, showed a rate of CD4$^+$ T cell decline (−31), that was within the range observed in LTA with a moderate CD4$^+$ T cell decline. Statistical analysis of the results obtained with the first available samples of the LTA and the progressor (dots in FIG. 1), showed that indeed only frequencies of Rev and Tat specific CTLp were significantly different between the two groups (Mann-Whitney p<0.0 and p<0.05, respectively). Rev specific CTLp were also significantly more prevalent in the LTA if only measurements of the first available samples collected within the first 24 months of follow-up, thus excluding those from L008 and L157, were included in this analysis (Mann-Whitney p<0.02). This result shows that the presence of Rev specific CTLp early after infection, is predictive of long-term AIDS-free survival. It is likely that the same holds true for Tat specific CTLp, although this could not be demonstrated conclusively due to the limited number of early Tat specific CTLp measurements obtained. The unexpected demonstration of Rev and Tat specific CTL in all LTA also contrasts their detection in 30 to 40% of unsolicited asymptomatic seropositive individuals observed by others (refs. 10 to 12).

In agreement with previous observations (refs. 9, 16), Gag specific CTLp were detected in all individuals of both groups. Interestingly, also Nef specific CTLp were detected in all individuals (ref. 10). The latter finding may reflect the over-representation of individuals expressing HLA-AL (67%) and HLA-A2 (83%). These molecules have been shown to present Nef epitopes (refs. 21, 22), and occur in 33% and 51% of blood donors in Amsterdam, respectively. RT was recognized by CTL from ten out of eleven individuals, which is in agreement with the percentages previously reported (refs. 5, 9).

Collectively, these human data indicated that Rev and Tat specific CTLs are directly involved in protection from disease progression and show the importance of Rev and Tat as major targets for inducing a protective CTL mediated immunity. Thus, in the asymptomatic stage, a considerable proportion of infected cells, both in circulation and in lymph nodes, do not produce virus (refs. 23, 24). They do, however, express multiple spliced mRNA from which both proteins Rev and Tat can be expressed (refs. 23 to 25), allowing the Rev and Tat specific CTL to eliminate latently infected cells. The early expression of Rev and Tat during virus replication (refs. 25, 26) allows specific CTL to kill productively infected cells, before release of progeny virus (refs. 12, 27, 28).

Considering the degree of matching of HLA class I phenotypes between LTA and progressors, variation in viral sequences may have a major impact on the formation of functional HLA-epitope complexes. In this regard, differences were found in the Rev sequences of viruses obtained from LTA L658 and progressor P424 who differed markedly in their CTL response to Rev but were serologically identical for all HLA class I and class II alleles tested (Table 2 below). Anchor residues of one HLA-AL peptide binding motive were found in viral sequences of L658 but not of P424.

Although these considerations would appear to also hold true for Nef specific CTL, their presence did not correlate with AIDS free survival and provides further evidence of the unexpected nature of the present discovery. Data obtained from studies in SIV$_{mae}$ infected macaques indicate that also in macaques Rev specific CTL responses inversely correlate with disease progression.

Vaccine Preparation and Use

It has been shown that an immunogenic preparation in accordance with the invention can elicit an immune response and, in particular, a cytotoxic T-cell response specific for Rev and/or Tat HIV proteins. One possible use of the present invention is, therefore, as the basis of a vaccine against immunodeficiency diseases including AIDS and AIDS-related conditions, comprising an immunogenic composition in accordance with the invention.

Vaccines may be prepared as injectables, as liquid solutions or emulsions. The immunogens may be mixed with pharmaceutically-acceptable excipients which are compatible therewith. Excipients may include water, saline, dextrose, glycerol, ethanol, and combinations thereof. The vaccine may further contain auxiliary substances, such as wetting or emulsifying agents, pH buffering agents, or adjuvants to enhance the effectiveness of the vaccines. Methods of achieving an adjuvant effect for the vaccine include the use of agents, such as aluminum hydroxide or phosphate (alum), commonly used as 0.05 to 0.1 percent solution in phosphate buffered saline and other adjuvants, including QS21, ISCOMs, Quil A, derivatives and components thereof, calcium phosphate, calcium hydroxide, zinc hydroxide, a glycolipid analog, an octadecyl ester of an amino acid, a muramyl dipeptide polyphosphazare, ISCOPRP, DC-chol, DDBA and a lipoprotein and other adjuvants to induce a Th1 response as well as incomplete Freund's adjuvant. Vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients, such as pharmaceutical grades of saccharine, cellulose and magnesium carbonate. These compositions take the form of solutions, suspensions, tablets, pills, capsules, sustained-release formulations or powders and contain 10 to 95% of the materials eliciting the cytotoxic T-cell response.

The vaccines are administered in a manner compatible with the dosage formulation, and in such amount as is therapeutically effective, protective and immunogenic. The quantity to be administered depends on the subject to be treated, including, for example, the capacity of the individual's immune system to synthesize antibodies, and to produce a cell-mediated immune response. Precise amounts of active ingredient required to be administered depend on the judgment of the practitioner. However, suitable dosage ranges are readily determinable by one skilled in the art and may be of the order of micrograms of the immunogens. Suitable regimes for initial administration and booster doses are also variable, but may include an initial administration followed by subsequent administrations. One example of an immunization schedule is at least one pre-immunization with an immunogen effective to produce a Rev and/or Tat-specific cytotoxic T-cell response, according to the present invention followed by at least one secondary immunization with a synthetic peptide described in published European Patent Publication Number 0 570 980, or a non-infectious retrovirus-like particle as described in U.S. Pat. No. 5,439,809 and published PCT Applications WO 96/05292 and WO 96/06177, each of which is incorporated herein by reference thereto. The dosage of the vaccine may also depend on the route of administration and will also vary according to the size of the host.

Nucleic acid molecules encoding the at least one cytotoxic T-cell epitope of the Rev and/or Tat proteins of the present invention may also be used directly for immunization by administration of the nucleic acid molecules directly, for example by injection to a host. Processes for the direct injection of DNA into test subjects for genetic immunization are described in, for example, Ulmer et al (ref. 30).

Molecules in accordance with the invention may further find use in the treatment (prophylactic or curative) of AIDS and related conditions.

A further aspect of the invention thus provides a method for the prophylaxis or treatment of AIDS or related conditions, comprising administering an effective amount of an immunogenic composition in accordance with the invention.

Generation of Rev and Tat specific Cytotoxic T Cell Responses

Methods for generating cytotoxic T cell responses are known to those skilled in the art. They include the construction and administration of viral vectors, such as Pox vector, including vaccinia containing a nucleic acid molecule encoding at least one cytotoxic T cell epitope from the Rev and/or Tat proteins. Such vectors are described in, for example, Moss (reference 32), Baxby (reference 33), G önczol (ref. 34). Other viral vectors include adenovirus (ref. 35) and Semliki virus (ref.47). In addition, bacterial vectors (ref. 36) and mycobacteria (including BCG) (ref. 37) may be used. Nucleic acid DNA immunization also may be used (ref. 38).

In addition, the cytotoxic T-cell response may be achieved by administering an immunogen containing a cytotoxic T-cell epitope. Such immunogen may be in the form of the protein or immunogenic fragment thereof or a peptide having an amino acid sequence corresponding to the T-cell epitope or a homolog of such protein or peptide in which amino acids have been deleted, inserted or substituted without essentially detracting from the immunological properties thereof (ref. 39) which may be lipidated (ref. 40). Such peptides may be monomeric, multimeric or mixtures of two or more peptides. In addition, such proteins, protein fragments and peptides may be administered in the form of conjugate molecules. A further possibility is to employ a non-infectious immunogenic HIV-like particle (ref. 46).

A variety of adjuvants, such as QS21, Quil A and components thereof, DC chol, ISCOMS, liposomes, Virosomes and polyphosphazene, may be employed along with these various vectors (refs. 41, 42, 47). Other carrier systems, such as biodegradable microparticles (ref. 44) or antigen presenting cells (ref. 45), which may be pulsed with Rev specific cytotoxic T cell peptide. Alternatively, antigen presenting cells may be infected with Rev using the recombinant vectors described above.

The materials which are administered in order to generate Rev and Tat specific cytotoxic T cell responses also may be administered in conjunction with cytokines, including IFNγ, GM-CSF, IL-12 and the macrophage activating cytokines.

Immunization-Challenge in Relevant Animal Model

Simian Immunodeficiency Virus (SIV) is a similar retrovirus that causes an immunodeficiency disease in monkeys. SIV is genetically and biologically related to HIV. SIV infection of monkeys is that a relevant animal model for taking precaution and treatment approaches to HIV infection.

An immunization-challenge experiment was carried out in adult cynomolgus monkeys using Semliki Forest Virus (SFV) and Vaccinia Strain Ankaran (MVA) recombinant viruses expressing both Rev and Tat. Subsequently the monkeys were challenged with the homologous SIV and tested for the development of viraemia during 10 weeks post challenge.

On week 0 and week 4, two monkeys were vaccinated parenterally with 1.5 to $10 \times 10^8$ of the SFV-Rev/Tat recombinant virus, followed by an immunization of 1 to $5 \times 10^8$ MVA-Rev/Tat recombinant virus. The control monkeys were vaccinated in the same way with an SFV Lac-Z (141) and an MVA (335) control preparation.

At week 14 all four monkeys were challenged with 50 MID50 SIVmac32H(J5) cells intravenously.

Figure 2:
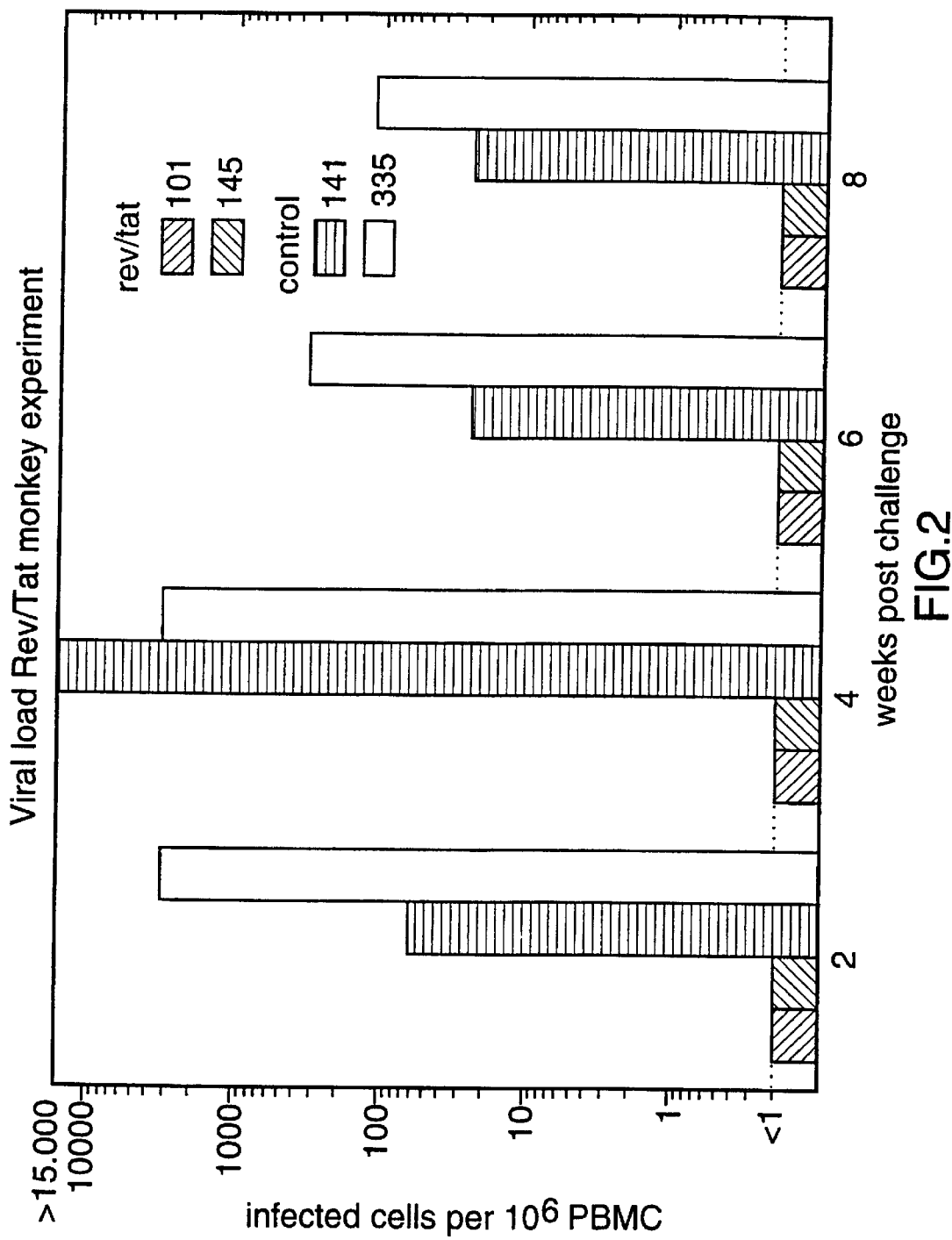
FIG. 2 is a graphical separation of the virus load in cynomolgus monkeys immunized with Rev/Tat recombinant virus, illustrating protection of the monkeys from simian immunodeficiency virus (SIV) infection.

Cell associated virus load was measured at weeks 2, 4, 6 and 10 post challenge. The results of the virus isolation are shown in FIG. 2. As may be seen in the data presented in FIG. 2, in the vaccinated monkeys, no infected cells were demonstrated during this observation period, whereas the sham-vaccinated monkeys showed cell-associated viraemia.

and four out of seven LTAs were seronegative at entry. Intervals between the last seronegative and first seropositive visit (seroconversion interval) were small allowing a well defined estimate of the time of seroconversion calculated as the midpoint between these two visits. AIDS defining symptoms, of the progressors were: Karposi's sarcoma (P493); Candida Albicans Oesophagitis (P1215, P424 and P039); and pneumocystis carinii pneumonia (P356). Rates of CD4$^+$ T cell decline (slopes) were calculated from CD4$^+$ T cell counts measured at regular three month interval during the entire follow-up period. Mean HIV-1 RNA load was determined using the NASBA technique. For L008 and P1215 AZT therapy was started at 109 and 51 months after entry, respectively, and DDC therapy was started at 126 and 69 months, respectively. The other individuals did not receive anti-viral therapy. Time points of PBMC sampling for CTLp frequency analyses and their corresponding CD4$^+$ T cell counts are indicated. HLA-A and -B phenotypes of the individuals were serologically determined at the Department Transplantation Immunology, CLB, Amsterdam.

TABLE I

| Individual* | HLA-phenotype A | B | Sero-status at Entry$^a$ | Sero-conversion interval (months) | Clinical Status (months after SC™ or E) AIDS | CD4 < 200$^b$ | Asymptomatic Follow-up | CD4 slope (cells ul$^{-1}$ month$^{-1}$) | Virus Load$^c$ (RNA copies ml$^{-1}$) | Sampling for CTL assays (months after SC or E) | Corresponding CD4 count (cells μl$^{-1}$) |
|---|---|---|---|---|---|---|---|---|---|---|---|
| L090 | 1.2 | 41.57 | I | 2.6 | NA | NA | >129 | +1.1 | <10$^3$ | 24 | 860 |
|  |  |  |  |  |  |  |  |  |  | 103 | 1160 |
| L658 | 1.2 | 8.61 | I | 3.3 | NA | NA | >110 | -1.3 | 8.3 × 10$^1$ | 4 | 950 |
|  |  |  |  |  |  |  |  |  |  | 69 | 690 |
| L211 | 1.2 | 8.57 | II | NA | NA | NA | >139 | -3.1 | nt | 24 | 730 |
|  |  |  |  |  |  |  |  |  |  | 74 | 710 |
| L709 | 1.69 | 14.57 | I | 3.4 | NA | NA | >122 | -3.5 | 2.5 × 10$^3$ | 8 | 850 |
|  |  |  |  |  |  |  |  |  |  | 84 | 770 |
| L434 | 2.28 | 7.27 | I | 3.0 | NA | NA | >129 | -3.7 | 7.4 × 10$^3$ | 8 | 630 |
| L008 | 2.26 | 27.44 | II | NA | NA | 132 | >140 | -4.5 | nt | 97 | 490 |
| L157 | 3.28 | 13.14 | II | NA | NA | 130 | >139 | -5.6 | nt | 88 | 710 |
| P493 | 1.2 | 8.35 | I | 3.0 | 40 | 28 |  | -3.1 | 4.7 × 10$^1$ | 5 | 420 |
|  |  |  |  |  |  |  |  |  |  | 9 | 450 |
| P1215 | 1.2 | 7.8 | I | 3.0 | 72 | 50 |  | -4.4 | 3.2 × 10$^3$ | 5 | 310 |
|  |  |  |  |  |  |  |  |  |  | 62 | 280 |
| P356 | 2.28 | 27.38 | I | 3.0 | 41 | 38 |  | -7 | 1.9 × 10$^4$ | 13 | 420 |
| P424 | 1.2 | 8.61 | I | 10.6 | 43 | 46 |  | -14 | 4.0 × 10$^4$ | 15 | 510 |
| P039 | 1.2 | 8.44 | I | 3.4 | 39 | 39 |  | -19 | 7.4 × 10$^4$ | 4 | 870 |
|  |  |  |  |  |  |  |  |  |  | 15 | 730 |

*L: LTA; P: progressor. The number following L or P indicates number of participants in the Amsterdam Cohort Studies on AIDS. a. I: seronegative; II: seropositive.
™ SC: seroconversion; E. Entry; NA: not applicable. b. First time point at which CD4$^+$ T cell count was below 200 μl. c. mean serum viral RNA load in first year after seroconversion; nt: not tested.

SUMMARY OF THE DISCLOSURE

In summary of the disclosure, there is provided methods and compositions to induce a cytotoxic T-cell response against Rev and Tat proteins of an immunodeficiency virus (in particular HIV) to prevent infection by or disease associated with immunodeficiency virus infection. There is also provided a method of determining a favourable prognosis in an HIV-infected individual by determining the presence of Rev and Tat-specific cytotoxic T-cells in the individual. Modifications are possible within the scope of the invention.

Table Legends

Table 1. Characteristics of HIV-1 seropositive participants in the Amsterdam Cohort studies on AIDS. All progressor Table 2. HLA class I motifs of Rev sequences obtained from non-cultured PBMC of L658 and P424. These individuals share HLA-A1, 2; -B8, 40,61; -C2,7; -DR3,6,13; -DR52; -DQ1,2. We have sequenced 20 and 19 individual recombinant PCR clones generated from PCR amplification products of the individuals, respectively. Sequences were analysed for the presence of HLA-A1, 2 and B8, 61 peptide binding motifs (ref. 46). Motifs of HIV-1$_{Lai}$ Rev, which was used for CTL detection, are indicated for reference purposes. A HLA-A1 motif was present in all the 20 sequences of viruses obtained from L658. All 19 viral sequences obtained from P424 analysed lacked the tyrosine anchor residue at position 9 of this putative epitope. two peptide binding motifs for HLA-A2 and one for HLA-B8 were identified in Rev sequences from both individuals. No motifs for HLA-B61 were found. Notably, all the putative epitopes differed between L658 and P424, either at the anchor residues (HLA-A1) or outside these anchor residues (HLA-A2, HLA-B8).

TABLE II

| | HLA-A1 (X[ST]XXXXXXY) | | | | HLA-A2 (X[LM]XXXXXX[VL]) | | | |
| --- | --- | --- | --- | --- | --- | --- | --- | --- |
| | L658 | | P424 | | L658 | | P424 | |
| | seq. | freq. | seq. | freq. | seq. | freq. | seq. | freq. |
| Lai | ISERILSTY[(1)] | 16/20 yes* | ISERILSTY[(4)] | yes | YLGQSAEPV[(7)] | yes | YLGRSAEPV[(10)] | yes |
| | L.GWL...[(2)] | 4/20 yes | ..GW...TS[(5)] | 15/19 no | ........[(7)] | 20/20 yes | S....K..[(11)] | 19/19 yes |
| | L.GWLL..[(3)] | yes | ..GW...NS.[(6)] | 4/19 no | | | | |
| Lai | | | | | ILVESPTVL[(8)] | yes | ILVESPTVL[(8)] | yes |
| | | | | | ........[(8)] | 19/20 yes | .....E...[(12)] | 18/19 yes |
| | | | | | ........A.[(9)] | 1/20 yes | ...G..E..[(13)] | 1/19 yes |

| | HLA-B8(XX[KR]X[KR]XXX[L]) | | | |
| --- | --- | --- | --- | --- |
| | L658 | | P424 | |
| | seq | freq. | seq. | freq. |
| Lai | RWRBRQRQI[(14)] | yes | RWRBRQRQI[(14)] | yes |
| | ......[(14)] | 20/20 yes | ...Q...[(15)] | 19/19 yes |
| Lai | | | | |

*Presence of motif.
[(1)]SEQ ID NO: 1
[(2)]SEQ ID NO: 2
[(3)]SEQ ID NO: 3
[(4)]SEQ ID NO: 4
[(5)]SEQ ID NO: 5
[(6)]SEQ ID NO: 6
[(7)]SEQ ID NO: 7
[(8)]SEQ ID NO: 8
[(9)]SEQ ID NO: 9
[(10)]SEQ ID NO: 10
[(11)]SEQ ID NO: 11
[(12)]SEQ ID NO: 12
[(13)]SEQ ID NO: 13
[(14)]SEQ ID NO: 14
[(15)]SEQ ID NO: 15

References

1. M. R. Klein, F. Miedema, *Trends in Microbiology* 3, 386 (1995).
2. I. P. M. Keet. et al, *AIDS* 7, 51 (1993).
3. B. F Haynes, G. Pantaleo, A. S. Fauci, *Science* 271, 324 (1996)
4. D. F. Nixon et al., *Nature* 336, 484 (1988).
5. B. D. Walker et al, *Science* 240, 64 (1988).
6. F. Buseyne et al., *J. Virol.* 67. 694 (1993).
7. Y. Riviere et al, *J. Virol.* 63, 2270 (1989).
8. R. A. Koup et al, *Blood* 73, 1909 (1989).
9. R. P. Johnson, B. D. Walker, *Curr. Top. Microbiol. linmunol.* 189, 35 (1994)
10. S. Lamhamedi-Cherradi et al, *AIDS* 6, 1249 (1992).
11. S. Lamhamedi-Cherradi et al, *AIDS* 9, 421 (1995).
12. Y. Riviere, M. N. Robertson, F. Buseyne, *Curr. Top Microbiol. Immunol.* 189, 65 (1994).
13. C. Rinaldo et al. *J. Virol* 69, 5838 (1995)
14. A. Carmichael, X. Jin, P Sissons, I Borysiewicz, *J. Exp. Med.* 177, 249 (1993).
15. R. A. Koup et al., *Journal of Virology* 68, 4650 (1994).
16. M. R. Klein et al, *J. Exp. Med.* 181, 1365 (1995).
17. A M. Geretti et al, *J. Inf. Dis.* 174, 34 (1996).
18. J. W. Mellors, et al, *Science* 272, 1167 (1996).
19. S. Jurriaans, et al, *Virol.* 204, 223 (1994); E. Hogervorst, et al, *J. Infect. Dis.* 171, 811 (1995); J. W. Mellors, et al, *Ann. Intern. Med.* 122, 573 (1995); D. R. Henrard, et al, *JAMA* 274, 554 (1995); K. Sasela, S. E. Stevens, P. Rubinstein, P. E. Taylor, D. Baltimore, *Ann. of Intern. Med.* 123, 641 (1995).
20. C. A. van Baalen, et al, *AIDS* 7, 781 (1993).
21. B. Culmann-Penciolelli el al, *J Virol.* 69, 618 (1995).
22. B. Culmann et al, *Eur. J. Immunol.* 19, 2382 (1989).
23. T. Seshamma, 0. Bagasra, D. Trono, D. Baltimore, R. J. Pomerantz, *Proc. Natl. Acad.*
24. J. Embretson et al. *Nature* 359 (1993).
25. T. Hope, R. J. Pomerantz, *Curr Top Microbiol.* Immunol. 193, 91 (1995).
26. A. Ranki, A. Lagerstedt, V. Ovod, E. Aavik, K. J. Krohn, *Arch Virol.* 139, 365 (1994).
27. V. Blazevic, A. Ranki, K. J. E. Krohn. *AIDS Res. Hum. Retroviruses* 11, 1335 (1995).
28. R. M. Zinkernagel, A. Althage, *J. Exp. Med.* 145, 644 (1977).
29. Ulmer et al., (1993) *Curr. Opinion Invest. Drugs.* 2 (9): 983–989.
30. Hope T., Pomerantz R. J., *Current topics in Microbiology and Immunology* 193: 91–105.
31. Gayner R. B 1995, *Current Topics in Microbiology and Immunology* 193: 51–77.
32. Moss B., *Science,* vol. 252, pp 1662–1667 (June, 1991).
33. D. Baxby et al., *Vaccine* Vol. 10, Issue 1, 1992.
34. E. Gönczol et al, *Vaccine,* vol. 13, No. 12, pp 1080–1085, 1995.
35. Jean-Lue Imler, *Vaccine* vol. 13, No. 13, pp 1143–1151, 1995.
36. M. B. Sztein et al., *The Journal of Immunology,* 1995, 155: pp 3987–3993.
37. A. Aldovini et al., *Nature* (1991), vol. 351: 479–482.
38. J. W. Shiver et al., *Annals New York Academy of Sciences,* pp 198–208.
39. S. K. Chai et al, *The Journal of Immunology,* vol. 149:2385–2390, No. 7, Oct. 1, 1992.

40. J. P. Sauzet et al., *Vaccine*, Vo. 13, No. 14, pp. 1339–1345, 1995.
41. F. Zhou et al., *The Journal of Immunology*, vol. 149, 1599–1604, No. 5, Sep. 1, 1992.
42. H. Takahashi et al., *Nature*, Vol. 344:873–875, 26 April 1990.
43. Voge et al., *Vaccine Design*, Ed. Powell et al, 1995, chapter 7, pp. 141–228.
44. A. Moore et al., *Vaccine*, vol. 13, No. 18, pp. 1741–1749, 1995.
45. Adams, S. E., *Vaccine Research*, vol. 2: 163–172, No. 3, 1993.
46. Rarmnensee, H. G., Friede, T. & Stevanoviic, S. (1995), *Immunogenetics* 41, 178–228.
47. Liljeström, P., *Biotechnology*, Vol. 9 (1991), 1356–1361.

What is claimed is:

1. A method of treatment of a host, which comprises:
   stimulating in the host a specific cytotoxic T-cell response which is specific for the Rev and/or Tat proteins of the immunodeficiency virus.

2. The method of claim 1 wherein the host is a human host and said immunodeficiency virus is human immunodeficiency virus.

3. The method of claim 2 wherein said cytotoxic T-cell response is stimulated by administering to the host at least one T-cell epitope selected from the Rev and Tat protein of HIV or a vector encoding the at least one cytotoxic T-cell epitope.

4. A method of treatment of a host, which comprises:
   selectively stimulating a protective Rev and/or Tat protein-specific cytotoxic T-cell response in said host.

5. The method of claim 4 wherein said immunodeficiency virus is human immunodeficiency virus and said host is a human host.

6. The method of claim 5 wherein said selective stimulation is effected by administering to the host at least one T-cell epitope selected from the Rev and Tat proteins of HIV.

7. The method of claim 6 wherein said at least one T-cell epitope is administered by administering the Rev and/or Tat HIV protein or a homolog thereof in which amino acids have been deleted, inserted or substituted without essentially detracting from the immunological properties thereof with a pharmaceutically-acceptable carrier therefor.

8. The method of claim 6 wherein said at least one T-cell epitope is administered by administering a synthetic peptide having an amino acid sequence corresponding to the T-cell epitope or a homolog thereof in which amino acids have been deleted, inserted or substituted without essentially detracting from the immunological properties thereof with a pharmaceutically-acceptable carrier therefor.

9. The method of claim 5 wherein said selective stimulation is effected by administering to the host a vector encoding at least one cytotoxic T-cell epitope selected from the Rev and Tat protein of HIV.

10. The method of claim 9 wherein said vector comprises a recombinant vector which expresses the Rev and/or Tat protein of HIV or a homolog thereof in which amino acids have been deleted, inserted or substituted without deviating from the immunological properties thereof.

11. At least one cytotoxic T-cell epitope selected from the Rev and Tat proteins of HIV or a vector encoding the at least one cytotoxic T-cell epitope when used as a medicament.

12. The T-cell epitope of claim 11 which is provided by the Rev and/or Tat protein of HIV or a homology thereof in which amino acids have been deleted, inserted or substituted without essentially detracting from the immunological properties thereof, in combination with a pharmaceutically-acceptable carrier.

13. The T-cell epitope of claim 11 which is provided by a recombinant vector or a nucleic acid molecule which expresses the Rev and/or Tat protein of HIV, or a homolog thereof in which amino acids have been deleted, inserted or substituted without essentially detracting from the immunological properties thereof.

14. The T-cell epitope of claim 11 which is provided by a synthetic peptide having an amino acid sequence corresponding to the T-cell epitope, or a homolog thereof in which amino acids have been deleted, inserted or substituted without essentially detracting from the immunological properties thereof, in combination with a pharmaceutical carrier therefor.

* * * * *